United States Patent [19]

Wong

[11] Patent Number: 4,892,831

[45] Date of Patent: Jan. 9, 1990

[54] INOCULATING DEVICE

[75] Inventor: Johnson N. S. Wong, Rolling Hills, Calif.

[73] Assignee: Evergreen Industries, Inc., Los Angeles, Calif.

[21] Appl. No.: 286,248

[22] Filed: Dec. 19, 1988

[51] Int. Cl.⁴ .............................................. C12M 1/26
[52] U.S. Cl. .................................... 435/292; 128/759; 422/100
[58] Field of Search ........................ 435/292, 294, 295; 128/757-759, 756, 304; 73/864.72; 422/68, 100; 433/142, 141, 143; 132/329

[56] References Cited

U.S. PATENT DOCUMENTS

| 2,925,087 | 2/1960 | Kucher | 132/329 |
| 3,485,236 | 12/1969 | Frost | 435/292 |
| 3,672,378 | 6/1972 | Silverman | 132/329 |
| 3,815,580 | 6/1974 | Oster | 435/292 |
| 4,102,748 | 7/1978 | Vacanti | 435/292 |
| 4,687,746 | 8/1987 | Rosenberg | 435/292 |
| 4,795,346 | 1/1989 | Takatsu | 433/141 |

FOREIGN PATENT DOCUMENTS 889461 2/1962 United Kingdom ................ 433/142

Primary Examiner—James C. Yeung
Attorney, Agent, or Firm—Nilsson, Robbins, Dalgarn, Berliner, Carson & Wurst

[57] ABSTRACT

An inoculating device having an inoculating loop, an improved streaking portion and a picker. The device is constructed of high impact polystyrene material which is injection molded to form a long thin member. One end of the device comprises a loop. The other end of the device forms a head having a plurality of distinct streaking surfaces. In the preferred embodiment, these distinct streaking surfaces have a convexity and come together to form a common point or apex, for example as in a curved pyramidal shape.

19 Claims, 2 Drawing Sheets

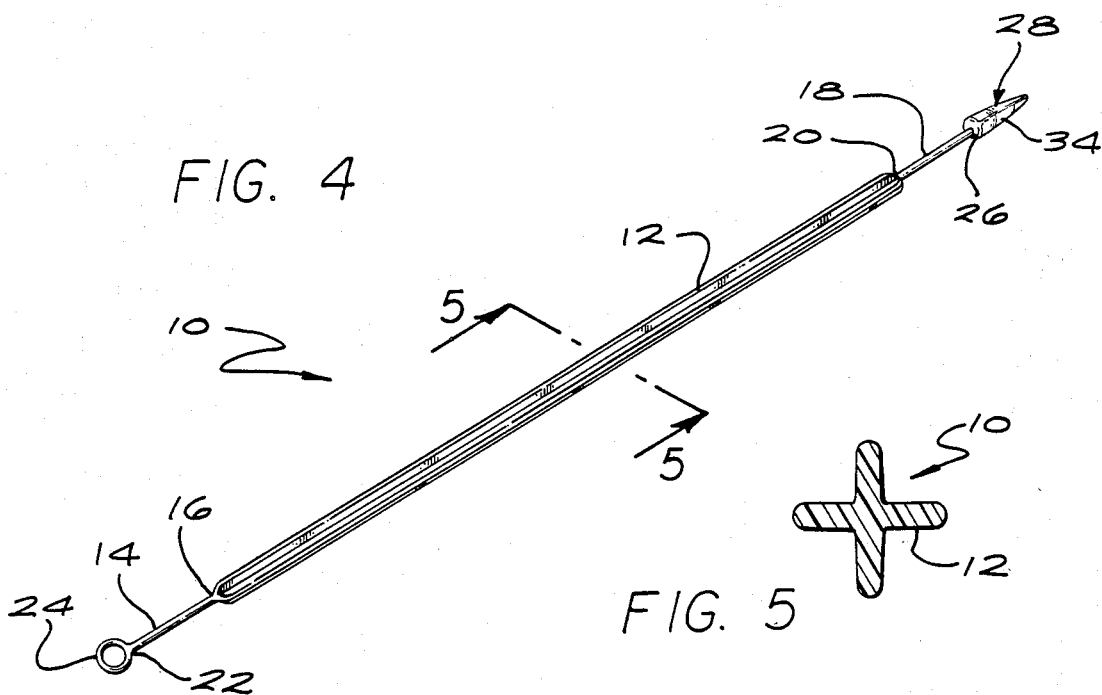
FIG. 4
FIG. 5
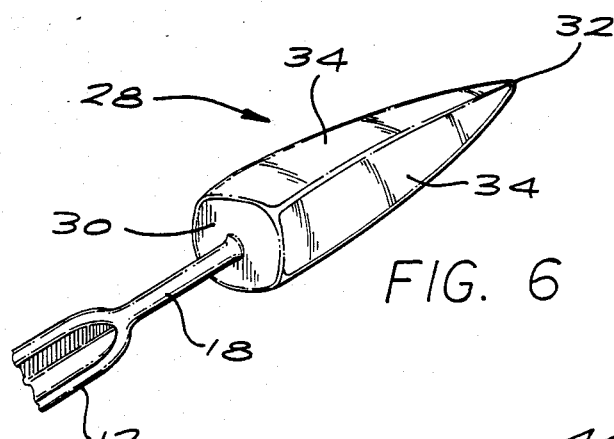
FIG. 6
FIG. 7
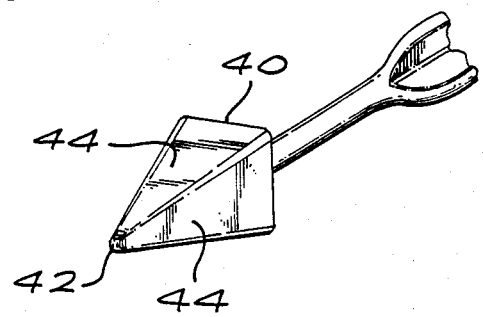
FIG. 8

INOCULATING DEVICE

FIELD OF THE INVENTION

This invention relates to bacteriological inoculating devices and, in particular, to a device which combines in a single integral unit an inoculating loop for transferring a quantitative bacteriological sample to a culture medium, an improved streaker for spreading the sample across the medium, and a built-in picker for selectively picking bacterial colonies when growth appears.

BACKGROUND OF THE INVENTION

Inoculating loops have been used to transfer bacteria from one medium to another, e.g. from pathogenic substances to a culture medium. In the past, the inoculating loop has been a long thin piece of wire looped at one end. The loop was usually made of platinum wire and was sterilized by exposing the wire to a heat source such as a flame or an electric heater.

Because the heating process and subsequent cooling of the loop was somewhat time consuming, disposable plastic inoculating loops were developed and used. The inexpensive plastic loops were used once and discarded, avoiding the step of resterilizing the loop. The use of plastic loops accordingly resulted in a time savings especially when processing large numbers of samples. Additionally, because a flame or heating unit was no longer required, inoculations could be done in places which were previously impractical, such as in the field, under hoods, in anaerobic chambers, in glove boxes, in doctors' offices and for satellite laboratory testing. Safety was also improved in that accidental fires were prevented and spattering of pathogenic substances, caused by heating the substance in a flame, was avoided. One of the early plastic loops is illustrated in FIG. 1. As shown, the device is simply a long thin member having a loop formed at one end.

An improvement made to the plastic inoculating loop is shown in FIG. 2. This device again has a loop formed at one end. The other end, however, is needle-shaped and used as a picker. The picker is used to selectively transfer a bacterial colony to another culture medium for further growth.

The prior art inoculating loop may also be used as a streaker. A streaker is used to spread bacteria on a culture medium, such as agar in a petri dish. In practice, a loopful of material is placed near one edge of the medium or agar and smeared back and forth to make a small but thickly smeared area which can then be studied to ascertain bacterial growth.

Because bacterial growth may be too excessive in the specified smeared area, it is sometimes necessary to prepare a less thickly smeared area in the petri dish. This is done by making a single stroke through the thickly smeared area, carrying this fresh stroke of material to an unused portion of the agar in the petri dish, and then streaking that single stroke of material along the unused portion of the agar. This process can be repeated as necessary. One disadvantage in using the loop itself for streaking is that it should be resterilized or replaced after preparing each smeared area. A clean loop for streaking insures a clear separation of bacteria on the agar from one smeared area to the next. However, the necessity of a clean loop results in either time consuming sterilization or excessive waste of plastic loops.

One prior art device developed to overcome this problem is depicted in FIG. 3. In this device, one end is formed in a loop and the other end has a spherical shape. The sphere may be used as a streaker and is an improvement over simply using the loop itself to streak because it allows the user to streak with an additional clean surface by rotating the sphere to an unused portion of its outer surface. This results in more efficient use of a single inoculating device.

The use of a sphere for streaking, however, also has disadvantages in that it does not always provide the clear separation of inoculum/bacteria desired. There is also a chance of carry-over and contamination from one portion of the sphere to another. Additionally, it is often difficult to determine what portion of the sphere has already been used.

Although there are a number of disposable plastic inoculating devices on the market as evidenced in FIGS. 1-3, none is able to effectively perform the functions of transferring, streaking and picking the sampled material. More than one of the devices is necessary to satisfy those functions resulting in excessive disposal and consequent waste of the used devices. In addition, the prior art streakers are also inadequate. As noted above, when preparing multiple and progressively less smeared areas, a clean surface is desired on the streaker for preparing each new area. The loop or needle is not adequate for this purpose because each should be replaced after each smeared area is complete to prevent contamination of any newly smeared area. The sphere, although an improvement, is also not guaranteed to provide a fresh sterile surface for each new smeared area desired.

SUMMARY OF THE INVENTION

The present invention overcomes the disadvantages of the prior art by combining in one device an inoculating loop, an improved streaking portion and a picker. The device is constructed of high impact polystyrene material which is injection molded to form a long thin member. One end of the device comprises a loop. The other end of the device forms a head having a plurality of distinct streaking surfaces. In the preferred embodiment, these distinct streaking surfaces have a convexity and come together to form a common point or apex, for example as in a curved pyramidal shape. The use of the pyramidal design provides both a plurality of distinct surfaces for streaking a sampled material and a point at the apex of the pyramid for selectively picking bacterial colonies when growth appears.

The distinct surfaces of the present invention are particularly advantageous when it is necessary to prepare a number of progressively thinner smeared areas in a culture medium which are then studied to ascertain bacterial growth. A fresh clean surface of the pyramid design is available to prepare each newly smeared area. Each distinct surface also provides a clear separation of bacteria with less chance of carryover or contamination upon one of the adjacent distinct surfaces. In addition, there is less waste as one device can be used for a plurality of smeared surfaces.

By having the distinct streaking surfaces come together to form a common point or apex, the device can be used to selectively transfer a bacterial colony to another culture medium for further growth. One of the distinct streaking surfaces can then be used to streak this colony of bacteria across the agar medium. All of this can be accomplished on the same pyramidal end of the device. Thus, having the picker and streaker in the same pyramidal end enhances the efficiency of the user/microbiologist.

Designing the distinct streaking surfaces to have a pyramidal form and adding a loop to the other end of the device, effectively combines in a single device an inoculating loop, a streaker and a picker. By combining all of the devices in one, the user may more efficiently go about performing the various tasks of transferring a sampled material, streaking the material on a culture medium and isolating selected portions as necessary. In addition, there is a subsequent reduction in waste due to the varied uses which may be performed of the present invention before a new sterilized device is required.

BRIEF DESCRIPTION OF THE DRAWINGS

FIG. 4 is a perspective view of one preferred embodiment of the present invention.

FIG. 5 is a cross-sectional view of the device shown in FIG. 4, taken along line 5—5.

FIG. 6 is an enlarged perspective view of the streaking portion of the device shown in FIG. 4.

FIG. 7 is an enlarged perspective view of a second preferred embodiment of the streaking portion of the present invention.

FIG. 8 is an enlarged perspective view of a third preferred embodiment of the streaking portion of the present invention.

DETAILED DESCRIPTION OF PREFERRED EMBODIMENTS

Figure 1:
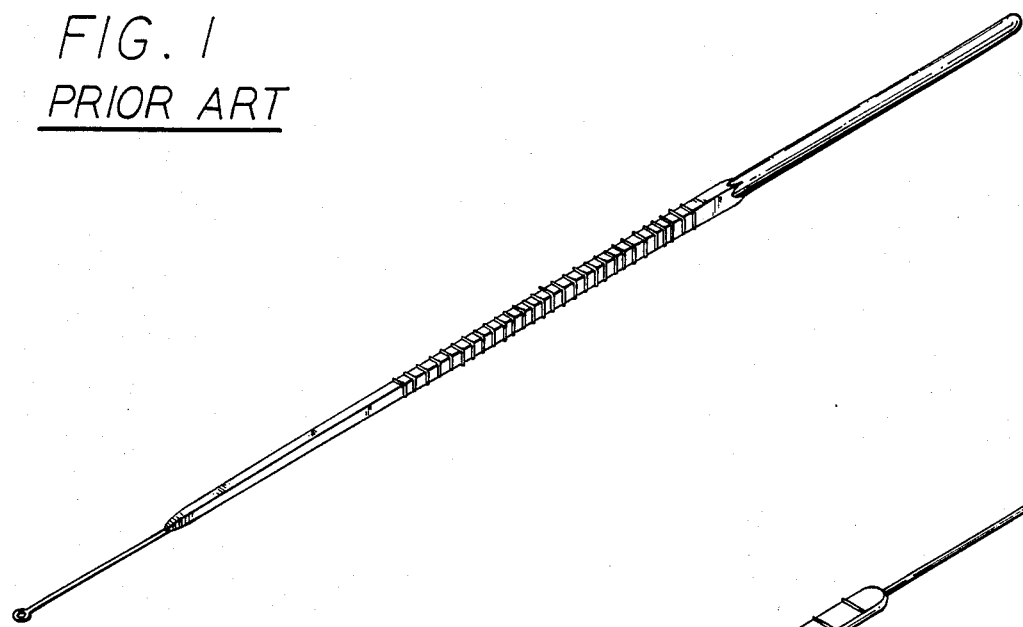
FIG. 1 is a perspective view of a prior art inoculating device.
Figure 2:
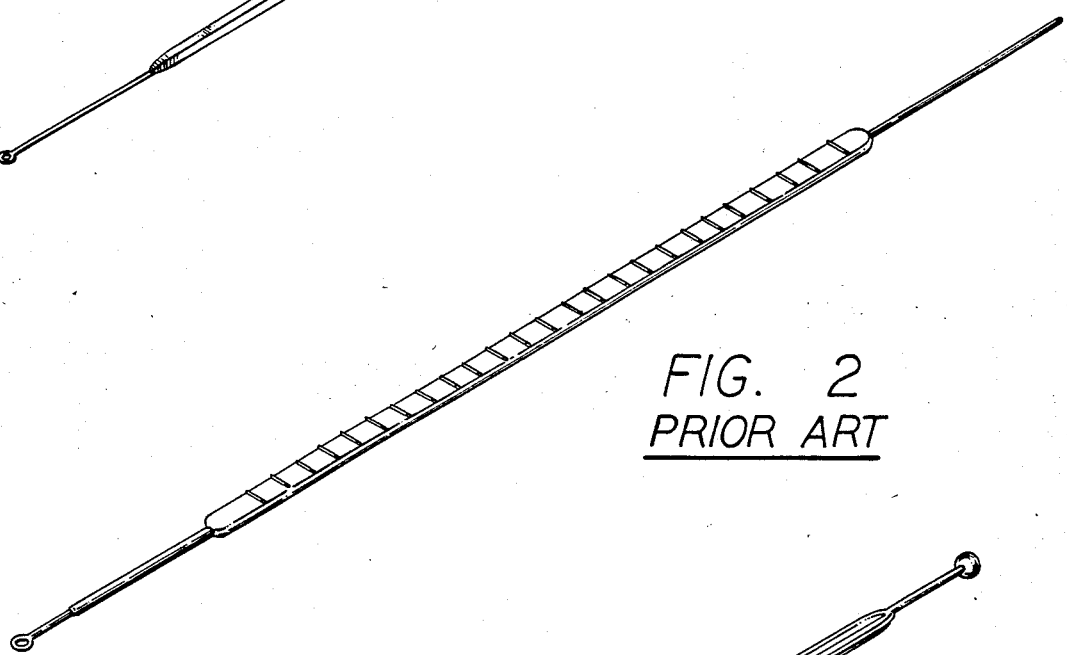
FIG. 2 is a perspective view of a prior art inoculating device having a picker.
Figure 3:
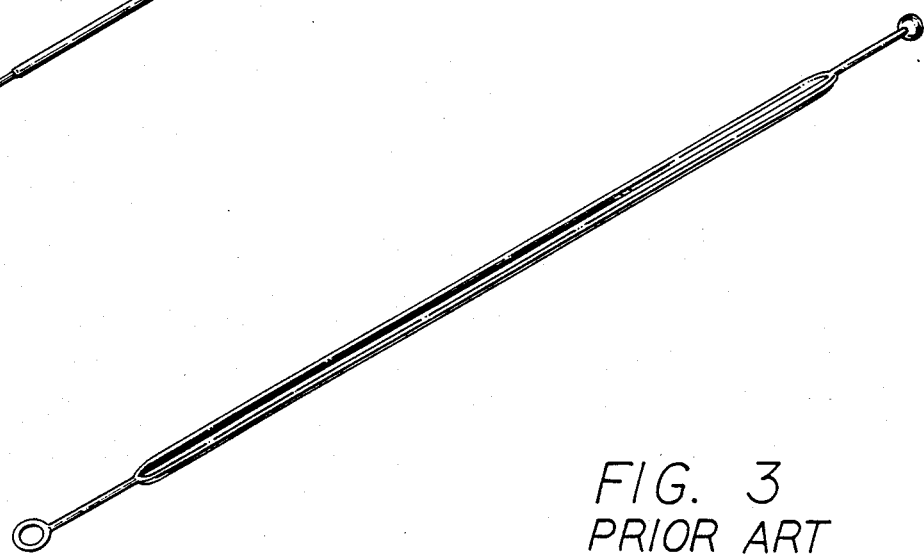
FIG. 3 is a perspective view of a prior art inoculating device having a spherical streaker.

An inoculating device embodying the features of the present invention is shown in FIG. 4, generally as 10. The device is injection molded with high impact polystyrene in one piece. Because the device is used for transferring bacterial samples to a culture medium for identifying the components of the sample, it should be sterilized, for example by gamma radiation.

The device 10 has a long thin handle 12. The handle 12 has a reduced cross-section, shown in FIG. 5, which reduces material costs and also reduces the time to cure the material when manufactured.

A first narrowed portion 14 is integrally connected at its inner end 16 to one end of the handle 12 and extends axially away from the handle. A second narrowed portion 18 is likewise integrally connected at its inner end 20 to the other end of the handle 12. The narrowed portions have a sufficient cross-section to allow them to resiliently and flexibly deflect when using the device.

The first narrowed portion 14 has an outer end 22 that is integrally connected to an inoculating loop 24. The loop 24 is of a predetermined size for transferring a known amount of material from one medium to another. Common sizes for inoculating loops are 1μl or 10μl.

The second narrowed portion 18 also has an outer end 26 which is connected to a curved pyramidal-shaped head 28 which serves as the streaking portion or picking portion of the device 10. Referring to FIG. 6, the head 28 has a four-sided base 30 and four distinct longitudinally extending surfaces 34. Each surface has a convexity in the longitudinal direction wherein all the surfaces 34 taper into a common point or apex 32. In addition, each surface 34 has a convexity in the lateral direction (i.e. a direction parallel to the intersection between the surface 34 and the base 30). Each side of the base 30 is similarly convex-shaped. The convexities help prevent cross-contamination between the surfaces during streaking.

As also shown in FIG. 6, the base 30 of the head 28 is integrally attached to the outer end 26 of the second narrowed portion 18. The apex 32 of the head 28 is disposed along the axis of the handle 12 of the device 10. preferably, each surface 34 has the same shape and surface area.

The curved pyramidal-shaped head 28 may be used as both a streaker and a picker. The four distinct convex-shaped surfaces 34 of the head 28 may each be used for streaking a sample on a medium, such as agar in a petri dish. The apex 32 of the head 28 may be used to isolate bacterial colonies or to remove the colonies from a culture medium. The apex 32 should not be so sharp as to make it dangerous to hold, however, it should be sleek enough to reach in between colonies and isolate them as desired. In addition, the corners between the base 30 and the surfaces 34 and between the surfaces 34 themselves, may be rounded to prevent damage to the medium or agar when streaking.

The advantages of the above described inoculating device are best illustrated by an example of how a microbiologist would use a single such device for a variety of purposes. First, a microbiologist uses the loop 24 of the device to pick up a known amount, for example 10μl, of a sample. The loopful of material is then deposited near one edge of the agar in a petri dish. The microbiologist then uses the other end of the device, namely one of the convex-shaped surfaces 34 of the head 28 to smear the sample material back and forth to make a small, but thickly smeared area on a portion of the agar. This thickly smeared area should not cover more than 1/5 of the total area of the plate. If it is desired to prepare successively thinner smeared areas of the sample on the agar, the same device is used. By rotating the device 90 degrees about its axis, a fresh clean convex-shaped surface 34 of the head 28 is used to prepare a less thickly smeared portion of the sample material on the agar. A single stroke is made with the fresh convex-shaped surface 34 through the thickly smeared area and the fresh stroke is carried back and fourth across an uninoculated portion of the agar on the plate, making 8 to 10 parallel lines about 0.5 to 1.0 cm apart. Rotating the device another 90 degrees again exposes another fresh clean convex-shaped surface 34 and another series of strokes may be made at right angles to the parallel lines previously prepared and about the same distance apart. This step is repeated as necessary.

It is important in making each newly smeared area, that the previously smeared areas not be touched when making the parallel lines. Also, it is important that the device be held at a point near its center of gravity. In this way, the pressure of the convex-shaped surface 34 on the agar is minimal and the agar is not cut. By rotating the device 90 degrees, a fresh clean surface for streaking is provided. This insures a clear separation of bacteria on the agar.

Once the sample medium has been streaked as desired and incubated, it is then studied for bacterial growth. During such studying, the apex 32 of the head 28 may be used, as necessary, to transfer a colony from the culture medium to inoculate another fresh culture medium to purify growth. The plurality of convex-shaped surfaces of the head 28 is then used to streak the inoculation as previously described. The microbiologist does this with the same device which was used to inoculate the medium and to streak it.

As shown above, the same device may be used to inoculate bacteria onto a culture medium and to prepare a plurality of smeared areas on the medium. Alternatively, the same device can be used to pick and transfer a bacterial colony from the culture medium to inoculate another culture medium and to streak the culture medium to purify the growth. A new device is not required for each step because a fresh clean sterilized surface is already available. Accordingly, the microbiologist may efficiently perform all of the above steps with a minimum number of devices, instead of disposing of and obtaining a new sterilized device for each of the above steps.

Although the curved pyramidal-shaped head provides optimum results for performing the streaking and picking functions, other shapes for the streaking portion of the device provide significant advantages over prior streaking devices. FIG. 7 depicts a second preferred embodiment of the invention wherein the streaking portion has a square base 40 and four equilateral triangular surfaces 44 which terminate in a point or apex 42. The triangular surfaces 44 of the streaking portion are formed at an angle of 30 degrees from the axis of the device 10. FIG. 8 shows a third preferred embodiment wherein the triangular surfaces 54 are formed at an angle of 45 degrees from the axis of the device.

In each of the preferred embodiments, the angle between the axis of the device and a line intersecting the apex and a point on the periphery of the base of the head should not be so small as to unduly reduce the cross-sectional area of the convex-shaped surfaces (FIG. 6) or the triangular surfaces (FIGS. 7 and 8) which would result in carryover and contamination from one surface to another during the streaking process. Conversely, the angle also should not be so great as to make the device clumsy or as to form an apex which is too bulky to effectively isolate bacterial colonies.

As shown in the above embodiments, the present invention discloses a single inoculating device which performs a variety of functions. The foregoing drawings and specifications merely are illustrative and describe preferred embodiments of the invention. Many structural changes are possible and those changes are intended to be within the scope of this disclosure. Other embodiments and variations will occur to those skilled in the art and they are contemplated to be within the scope of the claims.

What is claimed is:

1. A streaking device for use upon bacteriological samples comprising a handle, a first end of said handle and a pyramidal shaped head disposed on said first end, said pyramidal shaped head having a base, at least three distinct streaking surfaces which are convexly shaped in a lateral direction parallel to said base for streaking bacteriological samples, and an apex for isolating and transferring selected bacterial colonies from one culture medium to another.

2. The device of claim 1 wherein said streaking surfaces of said pyramidal shape are also convex-shaped in a longitudinal direction towards said apex.

3. The device of claim 1 wherein said head is nondeformable.

4. The device of claim 1 wherein said head is nonabsorbent.

5. The device of claim 1 wherein said pyramidal shaped head has exactly four streaking surfaces.

6. An inoculating device comprising a handle, a first end and a second end of said handle, an inoculating means for transferring a bacteriological sample from one medium to another disposed on said first end, and a head disposed on said second end having a plurality of distinct streaking surfaces that taper into a common apex to form a picking means for picking selected bacterial colonies.

7. The inoculating device of claim 6 wherein said streaking surfaces are planar.

8. The inoculating device of claim 6 wherein said streaking surfaces form a pyramidal shape and said pyramidal shape has a base disposed on said second end of said handle.

9. The inoculating device of claim 8 wherein said streaking surfaces of said pyramidal shape are convex-shaped in both the longitudinal and lateral directions.

10. The inoculating device of claim 8 wherein the base is square and the streaking surfaces of said pyramidal shape are planar equilateral triangles.

11. The inoculating device of claim 10 wherein the triangular streaking surfaces of said pyramidal shape are disposed at an angle in the range of 30 to 45 degrees from the axis of said handle.

12. The device of claim 8 wherein said inoculating means is an inoculating loop.

13. The inoculating device of claim 6 wherein said inoculating means is an inoculating loop and further comprising a resilient flexing means for permitting movement of said head and said inoculating loop with respect to said handle during use.

14. An inoculating device comprising a handle, a first end and a second end of said handle, an inoculating means for transferring a bacterial sample from one medium to another disposed on said first end, and a pyramidal type head, the base of said pyramidal type head disposed on said second end of said handle and the remaining surfaces of said pyramidal type head having a convexity.

15. The inoculating device of claim 14 wherein said handle has a longitudinal axis and the apex of said pyramidal type head is disposed along said axis of said handle, the base of said pyramidal type head is perpendicularly disposed on said second end of said handle.

16. The inoculating device of claim 14 wherein said remaining surfaces have a longitudinal convexity and a lateral convexity.

17. The inoculating device of claim 14 wherein the apex of said pyramidal type head is rounded so as not to puncture the skin of the user.

18. The inoculating device of claim 14 wherein said device is made of plastic and said pyramidal type head and inoculating means are integrally attached to said handle.

19. A disposable, plastic, integral, inoculating device comprising,
a handle having a first end, a second end, and a longitudinal axis;
first and second resilient flexing portions axially disposed on said first and second ends of said handle, respectively;
an inoculating loop disposed on said first flexing portion; and
a pyramidal shaped head having a base with four convex sides, four convexly-shaped surfaces extending from the base, and an apex, said base perpendicularly disposed on slaid second flexing portion, and said apex disposed along the longitudinal axis of said handle.

* * * * *